US010758517B2

(12) United States Patent
Tandon et al.

(10) Patent No.: US 10,758,517 B2
(45) Date of Patent: Sep. 1, 2020

(54) MPGES-1 INHIBITOR FOR THE TREATMENT OF OSTEOARTHRITIS PAIN

(71) Applicant: Glenmark Pharmaceuticals S.A., La Chaux-de-Fonds (CH)

(72) Inventors: Monika Tandon, New Delhi (IN); Sumit Sant, Thane (IN); Neelima Khairatkar-Joshi, Thane (IN); Girish Gudi, Mumbai (IN); Vinu C. A. Menon, Thane (IN); Ravi Talluri, Navi Mumbai (IN)

(73) Assignee: ICHNOS SCIENCES SA, La Chaux-de-Fonds (CH)

( * ) Notice: Subject to any disclaimer, the term of this patent is extended or adjusted under 35 U.S.C. 154(b) by 0 days.

(21) Appl. No.: 16/282,125

(22) Filed: Feb. 21, 2019

(65) Prior Publication Data

US 2019/0175562 A1 Jun. 13, 2019

Related U.S. Application Data

(63) Continuation of application No. PCT/IB2018/057244, filed on Sep. 20, 2018.

(30) Foreign Application Priority Data

Sep. 20, 2017 (IN) .............................. 201721033369
Nov. 27, 2017 (IN) .............................. 201721042452

(51) Int. Cl.
| | |
|---|---|
| *A61K 31/4196* | (2006.01) |
| *A61P 19/02* | (2006.01) |
| *A61K 9/16* | (2006.01) |
| *A61K 9/00* | (2006.01) |
| *A61K 9/14* | (2006.01) |

(52) U.S. Cl.
CPC ........ *A61K 31/4196* (2013.01); *A61K 9/0053* (2013.01); *A61K 9/14* (2013.01); *A61K 9/16* (2013.01); *A61P 19/02* (2018.01)

(58) Field of Classification Search
None
See application file for complete search history.

(56) References Cited

U.S. PATENT DOCUMENTS

| | | | |
|---|---|---|---|
| 9,096,545 B2 * | 8/2015 | Gharat | ................. C07D 401/10 |
| 9,439,890 B2 * | 9/2016 | Gharat | ................. C07D 413/12 |
| 9,949,955 B2 * | 4/2018 | Gharat | ............... A61K 31/5377 |

FOREIGN PATENT DOCUMENTS

| | | |
|---|---|---|
| WO | WO-2013186692 A1 | 12/2013 |
| WO | WO-2016016861 A1 | 2/2016 |

OTHER PUBLICATIONS

Gharat et al. in view of Li et al., Pharmaceutics, (2016), 8(17), p. 1-35.*
International Search Report issued in PCT/IB2018/057244, dated Dec. 19, 2018.

* cited by examiner

*Primary Examiner* — Yong L Chu
(74) *Attorney, Agent, or Firm* — Blank Rome LLP

(57) ABSTRACT

The present invention relates to a microsomal prostaglandin E synthases-1 ("mPGES-1") inhibitor for the treatment of osteoarthritis pain in a subject. For example, the present invention relates to a method of treating moderate osteoarthritis pain in a subject in need thereof by orally administering to the subject a substituted triazolone compound as a mPGES-1 inhibitor. The present invention also relates to pharmaceutical compositions comprising the mPGES-1 inhibitor, and to processes for preparing such pharmaceutical compositions.

17 Claims, 1 Drawing Sheet

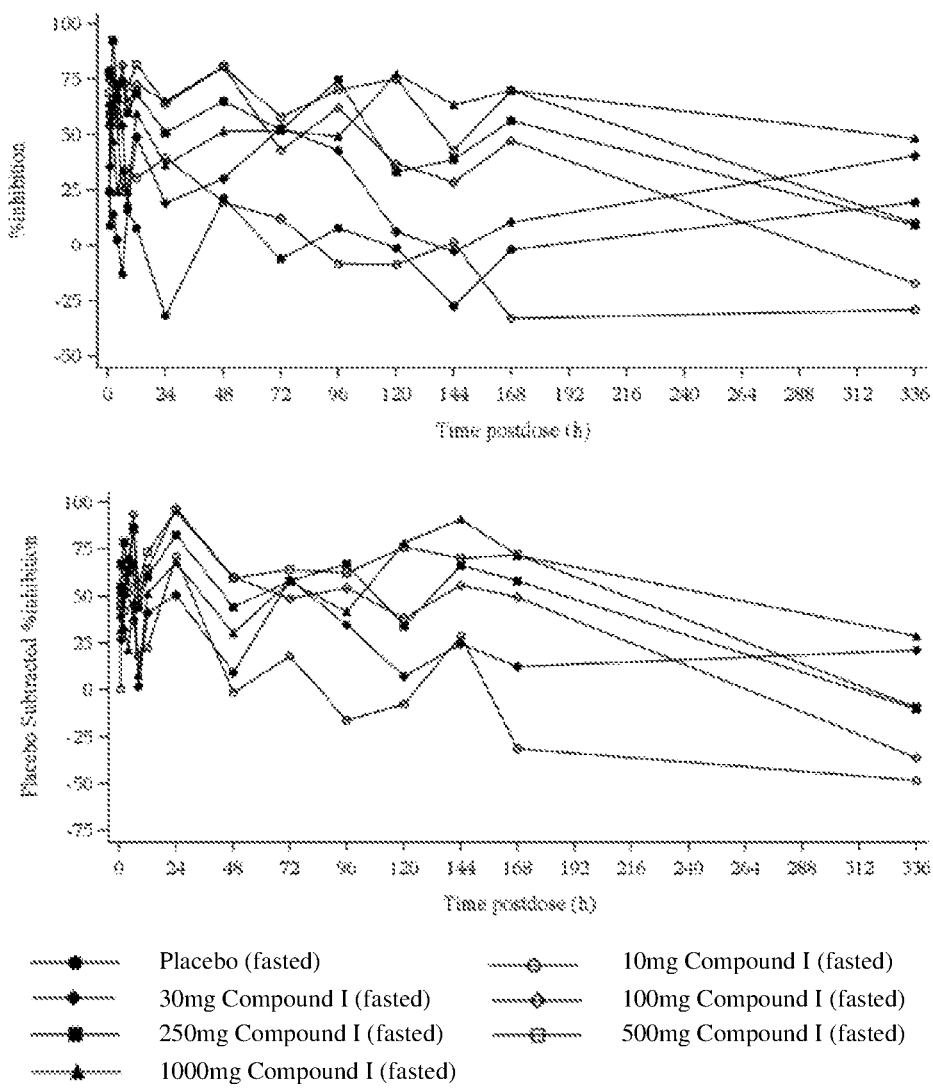

MPGES-1 INHIBITOR FOR THE TREATMENT OF OSTEOARTHRITIS PAIN

RELATED APPLICATIONS

This application is a continuation of International Application No. PCT/IB2018/057244, filed Sep. 20, 2018, which claims the benefit of Indian Provisional Application Nos. 201721033369, filed on Sep. 20, 2017, and 201721042452, filed on Nov. 27, 2017, each of which is hereby incorporated by reference in its entirety.

TECHNICAL FIELD OF THE INVENTION

The present invention relates to a microsomal prostaglandin E synthases-1 ("mPGES-1") inhibitor for the treatment of osteoarthritis pain in a subject. For example, in one embodiment, the present invention relates to a method of treating moderate osteoarthritis pain in a subject in need thereof by orally administering to the subject a substituted triazolone compound as a mPGES-1 inhibitor. The present invention also relates to pharmaceutical compositions comprising the mPGES-1 inhibitor, and to processes for preparing such pharmaceutical compositions.

BACKGROUND OF THE INVENTION

Inflammation is one of the common causes of many disorders including asthma, inflammatory bowel disease, rheumatoid arthritis, osteoarthritis, rhinitis, conjunctivitis and dermatitis. Inflammation also leads to pain. One of the major problems associated with existing treatments of inflammatory conditions is inadequate efficacy and/or the prevalence of side effects.

The enzyme cyclooxygenase (COX) converts arachidonic acid to an unstable intermediate, prostaglandin $H_2$ ($PGH_2$), which is further converted to other prostaglandins, including $PGE_2$, $PGF_{2\alpha}$, $PGD_2$, prostacyclin and thromboxane $A_2$. Among all prostaglandin metabolites, $PGE_2$ is particularly known to be a strong pro-inflammatory mediator, and is also known to induce fever and pain. The conversion of $PGH_2$ to $PGE_2$ by prostaglandin E synthases (PGES) may therefore represent a pivotal step in the propagation of inflammatory stimuli.

There are two microsomal prostaglandin E synthases (mPGES-1 and mPGES-2), and one cytosolic prostaglandin E synthase (cPGES). mPGES-1 is an inducible PGES after exposure to pro-inflammatory stimuli. mPGES-1 is induced in the periphery and central nervous system (CNS) by inflammation, and represents therefore a target for acute and chronic inflammatory disorders. $PGE_2$ is a major prostanoid, produced from arachidonic acid liberated by phospholipases (PLAs), which drives the inflammatory processes. Arachidonic acid is transformed by the action of prostaglandin H synthase (PGH synthase, cycloxygenase) into $PGH_2$ which is a substrate for mPGES-1, the terminal enzyme transforming $PGH_2$ to the pro-inflammatory $PGE_2$.

Agents that are capable of inhibiting the action of mPGES-1, and thus reducing the formation of the specific arachidonic acid metabolite $PGE_2$, are beneficial in the treatment of inflammation. Blocking the formation of $PGE_2$ in animal models of inflammatory pain results in reduced inflammation, pain and fever response (see, e.g., Kojima et. al., *The Journal of Immunology*, 2008, 180, 8361-6; Xu et. al., *The Journal of Pharmacology and Experimental Therapeutics*, 2008, 326, 754-63).

Osteoarthritis is a complex degenerative disease of joints characterized by progressive destruction of articular cartilage and peri-articular structures including bones, synovium, and associated fibrous joint tissues, and varying degrees of inflammation. Existing drug therapies can reduce pain associated with osteoarthritis, but may be only moderately effective over time and such therapies have a variable risk/benefit consideration. Current treatments using non-steroidal, anti-inflammatory drugs (NSAIDS) and/or Cyclooxygenase-2 inhibitors (COX-2 inhibitors) are efficacious, but can cause significant cardiovascular and gastrointestinal effects. Consequently, these classes of drugs may be contraindicated for many patients due to the patient's pre-existing or emergent cardiovascular and/or gastrointestinal conditions. Additionally, patients on these therapies can become refractory to specific drug treatments.

Thus, there still is a need for improved medications that can effectively treat musculoskeletal and connective tissue pain or inflammations and related symptoms. A medication that can provide long term control of musculoskeletal and connective tissue inflammations, inhibit further progress of existing conditions, and prevent reoccurrence of acute symptoms will have important medical significance for millions of people who suffer from these diseases International Publication Number WO 13/186692 discloses compounds which are shown to be mPGES-1 inhibitors. The publication discloses a compound N-(4-chloro-3-(5-oxo-1-(4-(trifluoromethyl)phenyl)-4,5-dihydro-1H-1,2,4-triazol-3-yl)benzyl)pivalamide, and pharmaceutically acceptable salts thereof. International Publication Number WO 16/016861 discloses nano-particulate formulations of N-(4-chloro-3-(5-oxo-1-(4-(trifluoromethyl)phenyl)-4,5-dihydro-1H-1,2,4-triazol-3-yl)benzyl)pivalamide. The entire contents of WO 13/186692 and WO 16/016861 are hereby incorporated by reference.

SUMMARY OF THE INVENTION

The present invention relates to a method of treating osteoarthritis pain in a subject in need thereof. In one embodiment, the method comprises administering to the subject a therapeutically effective amount of a mPGES-1 inhibitor.

In one embodiment, the present invention relates to a method of treating osteoarthritis pain in a subject in need thereof by administering to the subject a therapeutically effective amount of N-(4-chloro-3-(5-oxo-1-(4-(trifluoromethyl)phenyl)-4,5-dihydro-1H-1,2,4-triazol-3-yl)benzyl)pivalamide (also referred to as 'Compound I' hereinafter), or a pharmaceutically acceptable salt thereof.

In another embodiment, the present invention relates to a method of treating moderate osteoarthritis pain in a subject in need thereof by administering to the subject a therapeutically effective amount of N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof.

In yet another embodiment, the present invention relates to a method of treating osteoarthritis pain in a subject in need thereof by orally administering to the subject a therapeutically effective amount of N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof.

In yet another embodiment, the present invention relates to a method of treating osteoarthritis pain associated with hip and/or knee osteoarthritis in a subject in need thereof by orally administering to the subject a therapeutically effective amount of N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof.

A therapeutically effective amount of Compound I, or its pharmaceutically acceptable salt, to be administered (such as orally administered) per day is in the range from about 1 mg to about 1000 mg, preferably from about 10 mg to about 800 mg, or more preferably from about 10 mg to about 600 mg. In certain embodiments, the therapeutically effective amount of Compound I, or its pharmaceutically acceptable salt, is about 10 mg, about 25 mg, about 30 mg, about 50 mg, about 75 mg, about 90 mg, about 100 mg, about 120 mg, about 150 mg, about 180 mg, about 200 mg, about 250 mg, about 300 mg, about 350 mg, about 400 mg, about 450 mg, or about 500 mg. The therapeutically effective amount of Compound I, or its pharmaceutically acceptable salt, may be administered to the subject in the form of a pharmaceutical composition, such as an oral dosage form.

In additional embodiments, the effective amount of Compound I, or its pharmaceutically acceptable salt, may be administered (such as orally administered) once daily, or in divided doses, such as two, three, or four times a day. Preferably, Compound I, or its pharmaceutically acceptable salt, is administered (such as orally administered) once daily or twice daily. In a more preferred embodiment, Compound I is administered (such as orally administered) once daily.

In another embodiment, the present invention relates to a method of treating osteoarthritis pain in a subject in need thereof, the method comprising orally administering to the subject from about 1 mg to about 1000 mg of Compound I, or its pharmaceutically acceptable salt, per day.

In one embodiment, the present invention relates to a method of treating osteoarthritis pain in a subject in need thereof, the method comprising orally administering to the subject from about 1 mg to about 1000 mg of Compound I, or its pharmaceutically acceptable salt, per day, for a period of at least about 2, 4, 8, 10, or 12 weeks.

In one aspect of this embodiment, Compound I, or its pharmaceutically acceptable salt, is administered in an amount ranging from about 10 mg to about 800 mg, or from about 10 mg to about 600 mg daily. In another aspect of this embodiment, Compound I, or its pharmaceutically acceptable salt, is administered once daily or twice daily. In one preferred embodiment, the administration is once daily. In another embodiment, Compound I, or its pharmaceutically acceptable salt, is administered for a period of at least about 2, 4, 8, 10, or 12 weeks.

In another embodiment, the present invention relates to a method of treating osteoarthritis pain in a subject in need thereof comprising orally administering to the subject about 10 mg of Compound I, or its pharmaceutically acceptable salt. In one aspect of this embodiment, Compound I, or its pharmaceutically acceptable salt, is administered once daily or twice daily. For example, Compound I, or its pharmaceutically acceptable salt, is administered once daily. In another embodiment, Compound I, or its pharmaceutically acceptable salt, is administered for a period of at least about 2, 4, 8, 10, or 12 weeks.

In yet another embodiment, the present invention relates to a method of treating osteoarthritis pain in a subject in need thereof comprising orally administering to the subject about 25 mg of Compound I, or its pharmaceutically acceptable salt. In this embodiment, Compound I or its pharmaceutically acceptable salt is administered once daily or twice daily. For example, Compound I, or its pharmaceutically acceptable salt, is administered once daily. In another embodiment, Compound I, or its pharmaceutically acceptable salt, is administered for a period of at least about 2, 4, 8, 10, or 12 weeks.

In yet another embodiment, the present invention relates to a method of treating osteoarthritis pain in a subject in need thereof comprising orally administering to the subject about 75 mg of Compound I, or its pharmaceutically acceptable salt. In this embodiment, Compound I or its pharmaceutically acceptable salt, is administered once daily or twice daily. For example, Compound I, or its pharmaceutically acceptable salt, is administered once daily. In another embodiment, Compound I, or its pharmaceutically acceptable salt, is administered for a period of at least about 2, 4, 8, 10, or 12 weeks.

In yet another embodiment, the present invention relates to a method of treating osteoarthritis pain in a subject in need thereof comprising orally administering to the subject about 10 mg of Compound I, or its pharmaceutically acceptable salt, wherein Compound I, or its pharmaceutically acceptable salt, is administered once daily.

In yet another embodiment, the present invention relates to a method of treating osteoarthritis pain in a subject in need thereof comprising orally administering to the subject about 10 mg of Compound I, or its pharmaceutically acceptable salt, wherein Compound 1, or its pharmaceutically acceptable salt, is administered once daily for at least 12 weeks.

In yet another embodiment, the present invention relates to a method of treating osteoarthritis pain in a subject in need thereof comprising orally administering to the subject about 25 mg of Compound I, or its pharmaceutically acceptable salt, wherein Compound I, or its pharmaceutically acceptable salt, is administered once daily.

In yet another embodiment, the present invention relates to a method of treating osteoarthritis pain in a subject in need thereof comprising orally administering to the subject about 25 mg of Compound I, or its pharmaceutically acceptable salt, wherein Compound I, or its pharmaceutically acceptable salt, is administered once daily for at least 12 weeks.

In yet another embodiment, the present invention relates to a method of treating osteoarthritis pain in a subject in need thereof comprising orally administering to the subject about 75 mg of Compound I, or its pharmaceutically acceptable salt, wherein Compound I, or its pharmaceutically acceptable salt, is administered once daily.

In yet another embodiment, the present invention relates to a method of treating osteoarthritis pain in a subject in need thereof comprising orally administering to the subject about 75 mg of Compound I, or its pharmaceutically acceptable salt, wherein Compound I, or its pharmaceutically acceptable salt, is administered once daily for at least 12 weeks.

In another embodiment, the present invention relates to a method of treating osteoarthritis pain in a subject comprising orally administering to the subject Compound I, or its pharmaceutically acceptable salt, in the form of granules or as a tablet formulation at a dose level selected from about 10 mg, about 20 mg, about 25 mg, about 50 mg, about 75 mg and about 100 mg, once daily or twice daily, for a period of at least 2, 4, 8, 10, or 12 weeks. In a preferred embodiment, the method comprises orally administering to the subject Compound I, or its pharmaceutically acceptable salt, in the form of tablet formulation.

In one embodiment, Compound I, or a pharmaceutically acceptable salt thereof, is administered (e.g., 10 mg of Compound I, for example, to treat osteoarthritis pain) to a human subject (e.g., in a fasted state) such that (i) the $AUC_{0-inf}$ of Compound I is from about 13,680 to about 21,375 h*ng/mL, (ii) the $C_{max}$ of Compound I is from about 306.4 to about 478.75 ng/mL, (iii) the $T_{max}$ is from about 1.5 to about 4 hours, or (iv) any combination of any of the foregoing.

In another embodiment, Compound I, or a pharmaceutically acceptable salt thereof, is administered (e.g., 30 mg of Compound I, for example, to treat osteoarthritis pain) to a human subject (e.g., in a fasted state) such that (i) the $AUC_{0-inf}$ of Compound I is from about 36,400 to about 56,875 h*ng/mL, (ii) the $C_{max}$ of Compound I is from about 856 to about 1337.5 ng/mL, (iii) the $T_{max}$ is from about 1.5 to about 4 hours, or (iv) any combination of any of the foregoing.

In another embodiment, Compound I, or a pharmaceutically acceptable salt thereof, is administered (e.g., 100 mg of Compound I, for example, to treat osteoarthritis pain) to a human subject (e.g., in a fasted state) such that (i) the $AUC_{0-inf}$ of Compound I is from about 96,000 to about 150,000 h*ng/mL, (ii) the $C_{max}$ of Compound I is from about 1616 to about 2525 ng/mL, (iii) the $T_{max}$ is from about 2 to about 4 hours, or (iv) any combination of any of the foregoing.

In another embodiment, Compound I, or a pharmaceutically acceptable salt thereof, is administered (e.g., 100 mg of Compound I, for example, to treat osteoarthritis pain) to a human subject (e.g., in a fed state) such that (i) the $AUC_{0-inf}$ of Compound I is from about 129,600 to about 202,500 h*ng/mL, (ii) the $C_{max}$ of Compound I is from about 1712 to about 2675 ng/mL, (iii) the $T_{max}$ is from about 2 to about 4 hours, or (iv) any combination of any of the foregoing.

In another embodiment, Compound I, or a pharmaceutically acceptable salt thereof, is administered (e.g., 250 mg of Compound I, for example, to treat osteoarthritis pain) to a human subject (e.g., in a fasted state) such that (i) the $AUC_{0-inf}$ of Compound I is from about 156,800 to about 245,000 h*ng/mL, (ii) the $C_{max}$ of Compound I is from about 2312 to about 3612.5 ng/mL, (iii) the $T_{max}$ is from about 2 to about 4 hours, or (iv) any combination of any of the foregoing.

In another embodiment, Compound I, or a pharmaceutically acceptable salt thereof, is administered (e.g., 250 mg of Compound I, for example, to treat osteoarthritis pain) to a human subject (e.g., in a fed state) such that (i) the $AUC_{0-inf}$ of Compound I is from about 195,200 to about 305,000 h*ng/mL, (ii) the $C_{max}$ of Compound I is from about 2608 to about 4075 ng/mL, (iii) the $T_{max}$ is from about 4 to about 6 hours, or (iv) any combination of any of the foregoing.

In another embodiment, Compound I, or a pharmaceutically acceptable salt thereof, is administered (e.g., 500 mg of Compound I, for example, to treat osteoarthritis pain) to a human subject (e.g., in a fasted state) such that (i) the $AUC_{0-inf}$ of Compound I is from about 178,400 to about 278,750 h*ng/mL, (ii) the $C_{max}$ of Compound I is from about 3224 to about 5037.5 ng/mL, (iii) the $T_{max}$ is from about 3 to about 4 hours, or (iv) any combination of any of the foregoing.

In another embodiment, Compound I, or a pharmaceutically acceptable salt thereof, is administered (e.g., 1000 mg of Compound I, for example, to treat osteoarthritis pain) to a human subject (e.g., in a fasted state) such that (i) the $AUC_{0-inf}$ of Compound I is from about 156,800 to about 245,000 h*ng/mL, (ii) the $C_{max}$ of Compound I is from about 4424 to about 6912.5 ng/mL, (iii) the $T_{max}$ is from about 1.5 to about 4 hours, or (iv) any combination of any of the foregoing.

In one embodiment, Compound I, or a pharmaceutically acceptable salt thereof, is administered (e.g., 25 mg once daily Compound I, for example, to treat osteoarthritis pain) to a human subject such that (i) the mean $AUC_{0-24}$ of Compound I at steady state is from about 34,160 to about 51,240 h*ng/mL, (ii) the $C_{max}$ of Compound I at steady state is from about 1856 to about 2784 ng/mL, (iii) the $T_{max}$ is from about 1.5 to about 4 hours, or (iv) any combination of any of the foregoing.

In another embodiment, Compound I, or a pharmaceutically acceptable salt thereof, is administered (e.g., 75 mg once daily Compound I, for example, to treat osteoarthritis pain) to a human subject such that (i) the mean $AUC_{0-24}$ of Compound I at steady state is from about 62,320 to about 93,480 h*ng/mL, (ii) the mean C. of Compound I at steady state is from about 3576 to about 5364 ng/mL, (iii) the $T_{max}$ is from about 1.5 to about 4 hours, or (iv) any combination of any of the foregoing.

In any of the methods described herein, the method may further comprise determining the effect of Compound I on ex vivo LPS stimulated whole blood $PGE_2$ in healthy adult subjects.

In any of the methods described herein, the method may further comprise determining plasma and urine PK of Compound I following a single dose to elderly subjects.

In any of the methods described herein, the method may further comprise determining plasma PK of Compound I, following a single dose to healthy adult subjects.

In any of the methods described herein, the method may further comprise determining safety and tolerability of single dose of Compound I in healthy adult subjects.

In any of the methods described herein, the method may further comprise determining treatment-emergent adverse events (TEAEs) and serious adverse events (SAEs).

In any of the methods described herein, the method may further comprise determining dose-limiting toxicities (DLT).

In any of the methods described herein, the method may further comprise determining $AUC_{0-t}$, $AUC_{0-inf}$, $C_{max}$, $T_{max}$ under fed and fasting conditions.

In any of the methods described herein, the method may further comprise determining percent change from baseline on ex vivo whole blood $PGE_2$ synthesis after LPS stimulation in healthy subjects.

In any of the methods described herein, the method may further comprise determining the safety and tolerability of multiple oral doses of Compound I in healthy adult subjects.

In any of the methods described herein, the method may further comprise determining the safety and tolerability of multiple oral doses of Compound I in elderly subjects.

In any of the methods described herein, the method may further comprise determining plasma pharmacokinetics (PK) and cerebrospinal fluid (CSF) concentrations of Compound I following multiple doses to healthy adult subjects.

In any of the methods described herein, the method may further comprise determining the effect of multiple doses of Compound I on ex-vivo lipopolysaccharide (LPS)-stimulated whole blood prostaglandin $PGE_2$ in healthy adult subjects.

In any of the methods described herein, the method may further comprise determining the effect of multiple doses of Compound I on urinary markers of prostanoid metabolism in healthy adult subjects.

In any of the methods described herein, the method may further comprise determining the effect of multiple doses of Compound I on urine 6-beta hydroxyl cortisol/cortisol molar ratio and plasma 4-beta hydroxycholesterol in healthy adult subjects.

In any of the methods described herein, the method may further comprise determining plasma PK of Compound I following multiple doses in elderly subjects.

In any of the methods described herein, the method may further comprise determining effect of multiple doses of Compound I on urinary markers of prostanoid metabolism in elderly subjects.

In one embodiment, the present invention relates to a method of treating osteoarthritis pain in a subject, the method comprising orally administering to the subject a pharmaceutical composition comprising from about 1 mg to about 1000 mg of Compound I, or its pharmaceutically acceptable salt.

In another embodiment, the present invention relates to a method of treating osteoarthritis pain in a subject, the method comprising orally administering to the subject a pharmaceutical composition comprising about 10 mg to about 800 mg of Compound I, or its pharmaceutically acceptable salt.

In another embodiment, the present invention relates to a method of treating osteoarthritis pain in a subject, the method comprising orally administering to the subject a pharmaceutical composition comprising about 10 mg to about 600 mg, of Compound I, or its pharmaceutically acceptable salt.

In another embodiment, the present invention relates to a method of treating osteoarthritis pain in a subject, the method comprising orally administering to the subject a pharmaceutical composition comprising about 10 mg to about 100 mg, of Compound I, or its pharmaceutically acceptable salt.

In another embodiment, the present invention relates to a method of treating osteoarthritis pain in a subject, the method comprising orally administering to the subject a pharmaceutical composition comprising about 10 mg, or about 25 mg, or about 75 mg, of Compound I, or its pharmaceutically acceptable salt.

In another embodiment, the present invention relates to a method of treating osteoarthritis pain in a subject, the method comprising orally administering to the subject a pharmaceutical composition comprising about 10 mg of Compound I, or its pharmaceutically acceptable salt.

In another embodiment, the present invention relates to a method of treating osteoarthritis pain in a subject, the method comprising orally administering to the subject a pharmaceutical composition comprising about 25 mg of Compound I, or its pharmaceutically acceptable salt.

In another embodiment the present invention relates to a method of treating osteoarthritis pain in a subject, the method comprising orally administering to the subject a pharmaceutical composition comprising about 75 mg of Compound I, or its pharmaceutically acceptable salt.

In one aspect of this embodiment, the pharmaceutical composition is administered once daily or twice daily.

In another embodiment, the present invention relates to use of a therapeutically effective amount of Compound I, or its pharmaceutically acceptable salt, in the preparation of a pharmaceutical composition useful for oral administration for the treatment of osteoarthritis pain in a subject in need thereof.

In another embodiment, the present invention relates to a method of treating osteoarthritis pain in a subject, the method comprising orally administering to the subject a pharmaceutical composition comprising about 10 mg to about 100 mg, of Compound I, or its pharmaceutically acceptable salt once or twice daily for a period of at least about 2, 4, 8, 10, or 12 weeks.

In another embodiment, the present invention relates to a method of treating osteoarthritis pain in a subject, the method comprising orally administering to the subject a pharmaceutical composition comprising about 10 mg of Compound I, or its pharmaceutically acceptable salt once or twice daily for a period of at least about 2, 4, 8, 10, or 12 weeks.

In another embodiment, the present invention relates to a method of treating osteoarthritis pain in a subject, the method comprising orally administering to the subject a pharmaceutical composition comprising about 25 mg of Compound I, or its pharmaceutically acceptable salt once or twice daily for a period of at least about 2, 4, 8, 10, or 12 weeks.

In another embodiment, the present invention relates to a method of treating osteoarthritis pain in a subject, the method comprising orally administering to the subject a pharmaceutical composition comprising about 75 mg of Compound I, or its pharmaceutically acceptable salt once or twice daily for a period of at least about 2, 4, 8, 10, or 12 weeks.

In another embodiment, the present invention relates to a method of administering a mPGES-1 inhibitor for relieving osteoarthritis pain in a subject in need thereof, the method comprising administering a therapeutically effective amount of Compound I, or its pharmaceutically acceptable salt. In one aspect, the therapeutically effective amount of Compound I, or its pharmaceutically acceptable salt, is administered in a pharmaceutical composition suitable for oral administration.

In another embodiment, the present invention relates to a method of administering a nanoparticulate composition for the treatment of osteoarthritis pain in a subject in need thereof, the method comprising administering a therapeutically effective amount of compound I, or its pharmaceutically acceptable salt.

In any of the methods described herein, Compound I, or its pharmaceutically acceptable salt, may be administered to a subject in the fed or fasted state.

The pharmaceutical compositions described herein may contain about 10 mg, about 20 mg, about 25 mg, about 30 mg, about 50 mg, about 75 mg, about 90 mg, about 120 mg, about 150 mg, about 180 mg, about 200 mg, about 250 mg, about 300 mg, about 350 mg, about 400 mg, about 450 mg, or about 500 mg of Compound I, or its pharmaceutically acceptable salt. In one embodiment, the pharmaceutical compositions described herein contain about 10 mg, about 25 mg, or about 75 mg of Compound I, or its pharmaceutically acceptable salt.

The pharmaceutical compositions for oral administration described herein may be in various forms, for example, tablets, capsules, granules (synonymously, "beads" or "particles" or "pellets"), solution, suspension, emulsions, powders, dry syrups, and the like. In one embodiment, the pharmaceutical composition for oral administration is in the form of granules, tablets or capsules.

In one embodiment, the present invention provides a pharmaceutical composition suitable for oral administration for the treatment of osteoarthritis pain in a subject in need thereof, the composition comprising from about 1 mg to about 1000 mg of Compound I, or its pharmaceutically acceptable salt. In additional embodiments, the composition comprises from about 10 mg to about 800 mg or from about 10 mg to about 600 mg of Compound I, or its pharmaceutically acceptable salt. In one aspect of this embodiment, the pharmaceutical composition is in the form of granules, tablets or capsules. In one aspect of this embodiment, the pharmaceutical composition is a nanoparticulate composition. The nanoparticulate composition of the present invention can be converted into a suitable pharmaceutical composition.

In another aspect, the pharmaceutical composition is administered once daily or twice daily. In another aspect, the pharmaceutical composition is administered once daily or twice daily for a period of at least 12 weeks, or at least 14 weeks.

In another embodiment, the present invention relates to a method of administering a nanoparticulate composition for the treatment of osteoarthritis pain in a subject in need thereof, the method comprising administering about 10 mg of compound I, or its pharmaceutically acceptable salt.

In another embodiment, the present invention relates to a method of administering a nanoparticulate composition for the treatment of osteoarthritis pain in a subject in need thereof, the method comprising administering about 25 mg of compound I, or its pharmaceutically acceptable salt.

In another embodiment, the present invention relates to a method of administering a nanoparticulate composition for the treatment of osteoarthritis pain in a subject in need thereof, the method comprising administering about 75 mg of compound I, or its pharmaceutically acceptable salt.

In one embodiment, the present invention relates to a nanoparticulate pharmaceutical composition suitable for oral administration for the treatment or relief of osteoarthritis pain in a subject in need thereof, the composition comprising from about 1 mg to about 1000 mg of Compound I, or its pharmaceutically acceptable salt, and one or more surface stabilizers. In this embodiment, the surface stabilizer is polymer or surfactant. In one embodiment, the surface stabilizer is a polymer selected from one or more from polyvinyl pyrrolidone, copovidone, hydroxypropyl cellulose, hydroxyethyl cellulose, hydroxypropylmethyl cellulose, polyethylene glycol, natural gums, cellulose derivatives and combinations thereof. In another embodiment, the surface stabilizer is a surfactant selected from poloxamer, polyoxyethylene sorbitan esters, polyethoxylated castor oil, glycerol monostearate, phospholipids, benzalkonium chloride, triethanolamine, sodium lauryl sulfate, docusate sodium, vitamin E TPGS, soya lecithin, or combinations thereof.

In another embodiment, the present invention relates to a nanoparticulate pharmaceutical composition suitable for oral administration for the treatment of osteoarthritis pain in a subject in need thereof, the composition comprising from about 1 mg to about 1000 mg of Compound I, or its pharmaceutically acceptable salt, and a surface stabilizer, the formulation having an effective average particle size in the range from about 20 nm to about 1000 nm. In other aspects of this embodiment, the effective average particle size is in the range from about 30 nm to about 800 nm, from about 50 nm to 600 nm, from about 70 nm to about 500 nm, or from about 100 nm to 400 nm.

In another embodiment, the present invention provides a pharmaceutical composition suitable for oral administration for the treatment of osteoarthritis pain in a subject in need thereof, the composition comprising from about 1 mg to about 1000 mg of Compound I, or its pharmaceutically acceptable salt. In one aspect, a subject has preserved peripheral nerve function. In one aspect, the composition comprises from about 10 mg to about 800 mg or from about 10 mg to about 600 mg of Compound I, or its pharmaceutically acceptable salt. In one aspect of this embodiment, the pharmaceutical composition is in the form of granules, tablets or capsules. In another aspect of this embodiment, the pharmaceutical composition is a nanoparticulate composition. In another aspect of this embodiment, the pharmaceutical composition is administered once daily or twice daily. In another aspect of this embodiment, the pharmaceutical composition is administered once daily or twice daily for a period of at least 2, 4, 8, 10, 12 weeks.

In another embodiment, the present invention provides a pharmaceutical composition suitable for oral administration for the treatment of osteoarthritis pain in a subject in need thereof, the composition comprising about 10 mg of Compound I, or its pharmaceutically acceptable salt. In one aspect of this embodiment, the pharmaceutical composition is in the form of granules, tablets or capsules. In another aspect of this embodiment, the pharmaceutical composition is a nanoparticulate composition. In another aspect of this embodiment, the pharmaceutical composition is administered once daily or twice daily. In another aspect of this embodiment, the pharmaceutical composition is administered once daily or twice daily for a period of at least 2, 4, 8, 10, or 12 weeks. In another aspect of this embodiment, the osteoarthritis pain is moderate osteoarthritis pain.

In another embodiment, the present invention provides a pharmaceutical composition suitable for oral administration for the treatment of osteoarthritis pain in a subject in need thereof, the composition comprising about 25 mg of Compound I, or its pharmaceutically acceptable salt. In one aspect of this embodiment, the pharmaceutical composition is in the form of granules, tablets or capsules. In another aspect of this embodiment, the pharmaceutical composition is a nanoparticulate composition. In another aspect of this embodiment, the pharmaceutical composition is administered once daily or twice daily. In another aspect of this embodiment, the pharmaceutical composition is administered once daily or twice daily for a period of at least 2, 4, 8, 10, or 12 weeks. In another aspect of this embodiment, the osteoarthritis pain is moderate osteoarthritis pain.

In another embodiment, the present invention provides a pharmaceutical composition suitable for oral administration for the treatment of osteoarthritis pain in a subject in need thereof, the composition comprising about 75 mg of Compound I, or its pharmaceutically acceptable salt. In one aspect of this embodiment, the pharmaceutical composition is in the form of granules, tablets or capsules. In another aspect of this embodiment, the pharmaceutical composition is a nanoparticulate composition. In another aspect of this embodiment, the pharmaceutical composition is administered once daily or twice daily. In another aspect of this embodiment, the pharmaceutical composition is administered once daily or twice daily for a period of at least 2, 4, 8, 10, or 12 weeks. In another aspect of this embodiment, the osteoarthritis pain is moderate osteoarthritis pain.

In yet another embodiment, the present invention relates to a method of treating osteoarthritis pain in a subject in need thereof, the method comprising orally administering to the subject an effective amount of Compound I, or its pharmaceutically acceptable salt, wherein the subject shows more than 30% reduction, such as more than 50% reduction, from baseline in the Western Ontario and McMaster's University Osteoarthritis Index 3.1 pain subscale (WOMAC-PS).

In any of the methods described herein, the method may further comprise determining efficacy by one or more of the following assessments:

Efficacy assessment of pain intensity experienced in the most severely affected hip or knee joint over the previous 24 hours are performed using WOMAC-3.1 pain subscale with 5-items (each using 0-100 VAS) and average pain severity is used for primary efficacy analysis.

Efficacy assessments include total WOMAC-3.1 index score including 3 subscales: pain (5 items), stiffness (2 items) and physical function (17 items) each using 0-100 VAS at baseline and weeks 2, 4, 8, 12 and 14.

Patient and physician (or investigator) global assessment of response is done using 0-4 point Likert scale at weeks 2, 4, 8, 12 and 14.

In any of the methods described herein, the method may further comprise determining efficacy by one or more of the following assessments:

Mean change from baseline in the Western Ontario and McMaster's University Osteoarthritis Index 3.1 pain subscale (WOMAC-PS) at the end of 12 weeks of treatment.

Mean change from baseline in the WOMAC-3.1 pain subscale at the end of 2, 4 and 8 weeks of treatment and at follow up (14 weeks).

Mean change from baseline in the WOMAC-3.1 physical function subscale (WOMAC-PFS) at the end of 2, 4, 8 and 12 weeks of treatment and at follow up (14 weeks).

Mean change from baseline in overall WOMAC-3.1 index at the end of 2, 4, 8 and 12 weeks of treatment and at follow up (14 weeks).

Mean change from baseline in the Patient Global Assessment of Response to Therapy (PGART) using 0-4 point Likert scale at the end of 2, 4, 8 and 12 weeks of treatment and at follow up (14 weeks).

Mean change from baseline in the Investigator Global Assessment of Response to Therapy (IGART) using 0-4 point Likert scale at the end of 2, 4, 8 and 12 weeks of treatment and at follow up (14 weeks).

Proportion of subjects discontinuing due to lack of efficacy and/or requiring rescue medication use for pain in affected joint.

Proportion of subjects meeting OMERACT-OARSI responder criteria at the end of 4 and/or 12 weeks.

Incidence of Treatment Emergent Adverse Events (TEAEs) and Serious Adverse Events (SAEs) (including AEs of special interest such as edema, hypertension, congestive heart failure, pulmonary edema, cardiac failure, pre-defined upper gastrointestinal (GI) events and cardiovascular (CV) events).

Maximum plasma concentration ($C_{max}$), time to attain $C_{max}$ ($T_{max}$) and area under the plasma concentration-time curve over the dosing interval ($AUC_{0-tau}$) for Compound I or its pharmaceutically acceptable salt on Day 1 and Day 85 based on the Pharmacokinetic Analysis Set (PKAS).

In the above embodiment, the subject is administered Compound I, or its pharmaceutically acceptable salt, at a dose level selected from about 10 mg, about 20 mg, about 25 mg, about 50 mg, about 75 mg, and about 100 mg, once daily or twice daily, for a period of at least 2, 4, 8, 10, 12 weeks.

In any of the methods described above, the subject may have the following characteristics: (1) the subject has not received any oral NSAIDs or other analgesic treatment for a period of at least 1 week or 2 weeks prior to treatment with Compound I or its pharmaceutically acceptable salt, and (2) the subject has moderate pain intensity defined as a minimum of 40 mm and a maximum of 74 mm on 0-100 Visual Analogue Scale (Pain Walking on a Flat Surface. WOMAC 3.1, Section A, Question 1) in the most severely affected joint. In another embodiment, the subject has the following characteristics: (1) a human male or female subject aged between 40-70 years and diagnosed with primary osteoarthritis of the hip or knee for at least 3 months in accordance with American College of Rheumatology (ACR) clinical and radiological criteria, (2) the subject has not received any oral NSAIDs or other analgesic treatment for a period of at least 1 week or 2 weeks prior to treatment with Compound I or its pharmaceutically acceptable salt, and (3) the subject has moderate pain intensity defined as a minimum of 40 mm and a maximum of 74 mm on 0-100 Visual Analogue Scale (Pain Walking on a Flat Surface. WOMAC 3.1, Section A, Question 1) in the most severely affected joint.

In another embodiment, the subject to be treated for osteoarthritis pain is characterized by the followings criteria:

A human male or female subject aged between 40-70 years and diagnosed with primary osteoarthritis of the hip or knee for at least 3 months in accordance with American College of Rheumatology (ACR) clinical and radiological criteria.

A subject, who has not received any oral NSAIDs or other analgesic treatment for a period of at least 1 week prior to screening, having moderate pain intensity defined as a minimum of 40 mm and a maximum of 74 mm on 0-100 Visual Analogue Scale (Pain Walking on a Flat Surface. WOMAC 3.1, Section A, Question 1) in the most severely affected joint.

A subject, who has received prior oral NSAIDs and/or other oral analgesic medication for at least 2 weeks at the time of screening, having moderate pain intensity defined as a minimum of 40 mm and a maximum of 74 mm on 0-100 Visual Analogue Scale (Pain Walking on a Flat Surface. WOMAC 3.1, Section A, Question 1) and a minimum increase of 15 mm compared to screening in the most severely affected joint.

In another embodiment, the subject to be treated for osteoarthritis pain does not exhibit the followings criteria:

A subject experiencing severe pain, defined as minimum of 75 mm on 0-100 Visual Analogue Scale (Pain Walking on a Flat Surface. WOMAC 3.1 Section A, Question 1) in the most severely affected joint.

A subject who has a history or presence of signs or symptoms suggestive of active peptic ulcer disease, gastrointestinal (GI) bleeding, chronic gastritis, inflammatory bowel disease, or chronic diarrhea.

A subject with known aspirin allergy or allergic reaction to non-steroidal anti-inflammatory drugs (NSAIDs) including asthma and urticaria.

A subject using NSAIDs, COX-2 inhibitors or aspirin (except aspirin up to 100 mg daily for cardio-protection) within previous 7 days of randomization.

A subject having a history of positive *H. pylori* test performed within 6 months before randomization and with no documented eradication.

A subject using oral, intra-articular or intramuscular corticosteroids or intra-articular hyaluronic acid within 12 weeks before randomization.

A subject having a history of myocardial infarction, coronary artery bypass grafting/percutaneous coronary intervention, unstable angina, stroke or transient ischemic attack, or congestive heart failure (CHF) with symptoms at rest or with minimal activity.

A subject having hypertension with or without antihypertensive treatment (defined as sitting diastolic blood pressure (BP)>90 mm Hg or sitting systolic BP>150 mm Hg) at screening.

A subject having type 1 diabetes mellitus or uncontrolled type 2 diabetes mellitus (defined as HbA1c>7% at screening).

A subject having inherited or acquired disorders in platelet function, bleeding or coagulation or requiring anticoagulation (except low dose aspirin for cardioprotection).

A subject having clinical laboratory test values which are significantly different from normal reference ranges and/or judged clinically significant by the physician or investigator, including, but not limited to:
(a) eGFR<80 ml/min/1.73 m$^2$ as determined by MDRD method.
(b) ALT or aspartate amino transferase (AST)≥2 times ULN, and/or serum total bilirubin≥1.5 times ULN, at screening.

A subject having clinically significant illness or disease as determined by medical history, vital signs, physical examinations, ECG, laboratory studies, and other tests performed within 28 days prior to drug administration, that is judged by the physician or investigator to be detrimental for patient's participation in the study or that may prevent the successful completion of the study. Any condition that, in the opinion of the physician or investigator, would interfere with evaluation of the study drug or interpretation of subject safety or study results A subject having a positive result for hepatitis B surface antigen or hepatitis C antibody at screening.

A subject known to be seropositive for human immunodeficiency virus (HIV).

A subject who is an employee of the clinical study site or any other individuals involved with the conduct of the study, or immediate family members of such individuals.

A subject having concurrent enrolment in another interventional clinical study or previous participation in another interventional clinical study within 3 months prior to screening or within 5 half-lives of the previous study drug.

A female subject who is pregnant or breastfeeding.

A subject having a history of alcohol or drug abuse or dependence that in the opinion of the physician or investigator is considered to interfere with the subject's participation in the study.

In one embodiment, the present invention relates to a method of treating osteoarthritis pain in a subject in need thereof by orally administering to the subject a therapeutically effective amount of N-(4-chloro-3-(5-oxo-1-(4-(trifluoromethyl)phenyl)-4,5-dihydro-1H-1,2,4-triazol-3-yl)benzyl)pivalamide, or its pharmaceutically acceptable salt, wherein the subject is diagnosed with primary osteoarthritis of the hip or knee for at least 3 months in accordance with American College of Rheumatology (ACR) clinical and radiological criteria.

In another embodiment, the present invention relates to a method of treating osteoarthritis pain in a subject in need thereof by orally administering to the subject a therapeutically effective amount of N-(4-chloro-3-(5-oxo-1-(4-(trifluoromethyl)phenyl)-4,5-dihydro-1H-1,2,4-triazol-3-yl)benzyl)pivalamide, or its pharmaceutically acceptable salt, wherein the subject has moderate pain intensity defined as a minimum of 40 mm and a maximum of 74 mm on 0-100 Visual Analogue Scale (Pain Walking on a Flat Surface. WOMAC 3.1, Section A, Question 1) in the most severely affected joint. In one aspect of this embodiment, the subject must have not received any oral NSAIDs or other analgesic treatment for a period of at least 1 week prior to screening.

In another embodiment, the present invention relates to a method of treating osteoarthritis pain in a subject in need thereof by orally administering to the subject a therapeutically effective amount of N-(4-chloro-3-(5-oxo-1-(4-(trifluoromethyl)phenyl)-4,5-dihydro-1H-1,2,4-triazol-3-yl)benzyl)pivalamide, or its pharmaceutically acceptable salt, wherein the subject has moderate pain intensity defined as a minimum of 40 mm and a maximum of 74 mm on 0-100 Visual Analogue Scale (Pain Walking on a Flat Surface. WOMAC 3.1, Section A, Question 1) and a minimum increase of 15 mm compared to screening in the most severely affected joint. In one aspect of this embodiment, the subject has received prior oral NSAIDs and/or other oral analgesic medication for at least 2 weeks at the time of screening.

In another embodiment, the present invention related to method of treating osteoarthritis pain in a subject in need thereof by orally administering a nanoparticulate pharmaceutical composition comprising about 10 mg to about 100 mg of N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof, wherein the subject has moderate pain intensity defined as a minimum of 40 mm and a maximum of 74 mm on 0-100 Visual Analogue Scale (Pain Walking on a Flat Surface. WOMAC 3.1, Section A, Question 1) in the most severely affected joint.

In another embodiment, the present invention related to method of treating osteoarthritis pain in a subject in need thereof by orally administering a nanoparticulate pharmaceutical composition comprising about 10 mg or about 25 mg or about 75 mg of N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof, wherein the subject has moderate pain intensity defined as a minimum of 40 mm and a maximum of 74 mm on 0-100 Visual Analogue Scale (Pain Walking on a Flat Surface. WOMAC 3.1, Section A, Question 1) in the most severely affected joint.

In another embodiment, the present invention related to method of treating osteoarthritis pain in a subject in need thereof by orally administering a nanoparticulate pharmaceutical composition comprising about 10 mg of N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof, wherein the subject has moderate pain intensity defined as a minimum of 40 mm and a maximum of 74 mm on 0-100 Visual Analogue Scale (Pain Walking on a Flat Surface. WOMAC 3.1, Section A, Question 1) in the most severely affected joint.

In another embodiment, the present invention related to method of treating osteoarthritis pain in a subject in need thereof by orally administering a nanoparticulate pharmaceutical composition comprising about 25 mg of N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof, wherein the subject has moderate pain intensity defined as a minimum of 40 mm and a maximum of 74 mm on 0-100 Visual Analogue Scale (Pain Walking on a Flat Surface. WOMAC 3.1, Section A, Question 1) in the most severely affected joint.

In another embodiment, the present invention related to method of treating osteoarthritis pain in a subject in need thereof by orally administering a nanoparticulate pharmaceutical composition comprising about 75 mg of N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof, wherein the subject has moderate pain intensity defined as a minimum of 40 mm and a maximum of 74 mm on 0-100 Visual Analogue Scale (Pain Walking on a Flat Surface. WOMAC 3.1, Section A, Question 1) in the most severely affected joint.

In yet another embodiment, the present invention relates to a method of treating osteoarthritis pain in a subject in need thereof by orally administering to the subject about 10 mg of Compound I, or its pharmaceutically acceptable salt, wherein the subject shows more than a 30% reduction, such as more than a 50% reduction from baseline in the Western Ontario and McMaster's University Osteoarthritis Index 3.1 pain subscale (WOMAC-PS). In one aspect of this embodiment, Compound I, or its pharmaceutically acceptable salt, is administered once daily or twice daily.

In yet another embodiment, the present invention relates to a method of treating osteoarthritis pain in a subject in need thereof by orally administering to the subject about 25 mg of Compound I, or its pharmaceutically acceptable salt, wherein the subject shows more than a 30% reduction, such as more than a 50% reduction from baseline in the Western Ontario and McMaster's University Osteoarthritis Index 3.1 pain subscale (WOMAC-PS). In one aspect of this embodiment, Compound I, or its pharmaceutically acceptable salt, is administered once daily or twice daily.

In yet another embodiment, the present invention relates to a method of treating osteoarthritis pain in a subject in need thereof by orally administering to the subject about 75 mg of Compound I, or its pharmaceutically acceptable salt, wherein the subject shows more than a 30% reduction, such as more than a 50% reduction, from baseline in the Western Ontario and McMaster's University Osteoarthritis Index 3.1 pain subscale (WOMAC-PS). In one aspect of this embodiment, Compound I, or its pharmaceutically acceptable salt, is administered once daily or twice daily. In one aspect of this embodiment, Compound I, or its pharmaceutically acceptable salt is administered as a pharmaceutical composition, once daily or twice daily.

In another embodiment, the present invention relates to a method of treating osteoarthritis pain in a subject, the method comprising orally administering to the subject a pharmaceutical composition comprising between about 10 mg and about 800 mg, such as between about 10 mg and about 600 mg, of Compound I, or its pharmaceutically acceptable salt.

In another embodiment the present invention relates to a method of treating osteoarthritis pain in a subject, the method comprising orally administering to the subject a pharmaceutical composition comprising about 75 mg of Compound I, or its pharmaceutically acceptable salt. In one aspect of this embodiment, the pharmaceutical composition is administered once daily or twice daily.

In another embodiment, the present invention relates to use of a therapeutically effective amount of Compound I, or its pharmaceutically acceptable salt, in the preparation of a pharmaceutical composition useful for oral administration for the treatment for osteoarthritis pain in a subject in need thereof.

In one embodiment, the present invention relates to a nanoparticulate pharmaceutical composition suitable for oral administration for the treatment or relief of osteoarthritis pain in a subject in need thereof; wherein composition comprising Compound I or its salt and a surface stabilizer, said formulation having an effective average particle size in the range from about 20 nm to about 1000 nm. In aspect of this embodiment, the effective average particle size is in the range from about 30 nm to about 800 nm, or from about 50 nm to 600 nm, or from about 70 nm to about 500 nm, or from about 100 nm to 400 nm.

BRIEF DESCRIPTION OF THE DRAWINGS

FIG. 1 shows the percentage inhibition from baseline of ex vivo LPS-stimulated $PGE_2$ concentration following single oral doses of Compound I in healthy fasted subjects as described in Example 1.

DETAILED DESCRIPTION OF THE INVENTION

The terms used herein are defined as follows. If a definition set forth in the present application and a definition set forth in a subsequent non-provisional application claiming priority to the present application are in conflict, the definition in the subsequent non-provisional application shall control the meaning of the terms.

The term "effective amount" or "therapeutically effective amount" denotes an amount of the mPGES-1 inhibitor (such as Compound I or its pharmaceutically acceptable salt) that, when orally administered to a subject produces a medically significant therapeutic benefit in a subject. The term "medically significant" is defined as at least a minimal medical benefit in the subject. The effective amount of Compound I, or its pharmaceutically acceptable salt, to be administered per day ranges from about 1 mg to about 1000 mg, such as from about 10 mg to about 800 mg or from about 60 mg to about 600 mg. Typically, the therapeutically effective amount of Compound I, or its pharmaceutically acceptable salt, may be about 10 mg, about 20 mg, about 25 mg, about 30 mg, about 50 mg, about 75 mg, about 90 mg, about 120 mg, about 150 mg, about 180 mg, about 200 mg, about 250 mg, about 300 mg, about 350 mg, about 400 mg, about 450 mg, or about 500 mg, although larger or smaller amounts are not excluded if they fall within the scope of the definition of this paragraph. For subjects who do not experience sufficient benefit with a certain dose, the dose may be further increased based on efficacy and tolerability. Further, if there is no evidence that such an increase in dose confers an additional benefit, the dose can be reduced.

The effective amount of Compound I, or its pharmaceutically acceptable salt, may be administered once daily, or in divided doses such as two, three of four times a day. For example, Compound I, or its pharmaceutically acceptable salt, may be administered once daily or twice daily.

The term "about" as used herein means an acceptable error for a particular value as determined by one of ordinary skilled in the art, which depends in part on how the value is measured or determined.

The term "active ingredient" (used interchangeably with "active," "active substance" or "drug") as used herein includes Compound I, or its pharmaceutically acceptable salt.

The term "salt" or "pharmaceutically acceptable salt", means those salts which are, within the scope of sound medical judgment, suitable for use in contact with the tissues of humans and lower animals without undue toxicity, irritation, and allergic response, commensurate with reasonable benefit to risk ratio, and effective for their intended use. Representative acid additions salts include, but are not limited to, hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, ascorbate, glucoheptonate, lactobionate, and lauryl sulphate salts. Representative alkali or alkaline earth metal salts include, but are not limited to, sodium, calcium, potassium and magnesium salts.

The term "nanoparticulate composition" as used herein refers to a pharmaceutical dispersion wherein drug particles are dispersed in a solvent and have an effective average particle size of less than about 1000 nm.

As an example, the phrase "an effective average particle size in the range from about 20 nm to about 1000 nm" means that at least 50% of the total particles of Compound I, or its pharmaceutically acceptable salt have an average particle size in the range from about 20 nm to about 1000 nm.

The term "treating" or "treatment" as used herein also covers prophylaxis, mitigation, prevention, amelioration, suppression, alleviation of symptoms, slowing the appearance of symptoms, slowing the progression of symptoms of a disease or disorder modulated by the mPGES-1 in a subject.

By the term "pain", it is meant any condition or disease related to pain that includes, but is not limited to, acute pain, chronic pain, mild pain, moderate pain, severe pain and can include nociceptive pain, inflammatory pain and pathological pain. Preferably, the pain includes osteoarthritis pain.

The term "osteoarthritis" means a chronic type of arthritis characterized by the breakdown of cartilage, the hard, slippery tissue that covers the ends of bones where they meet to form a joint. Unlike some other forms of arthritis, such as rheumatoid arthritis, osteoarthritis affects only joint function and does not affect skin tissue, the lungs, the eyes or the blood vessels. Healthy cartilage in a joint allows bones to glide over one another and also absorbs energy from the shock of physical movement. In osteoarthritis, the surface layer of cartilage breaks down and wears away. This breakdown of the cartilage allows the bones under the cartilage to rub together, causing pain, swelling, and loss of motion of the joint. Over time, the joint may lose its normal shape. Also, small deposits of bone, called osteophytes or bone spurs, may grow on the edges of the joint. Bits of bone or cartilage can break off and float inside the joint space. This causes more pain and damage to the joint and can cause stiffness and pain that make it difficult for a person having osteoarthritis to use that joint. Osteoarthritis can also damage ligaments and menisci. Over time osteoarthritis may create a need for joint replacements.

The term "osteoarthritis pain" means pain caused by osteoarthritis in a joint of a mammal, such as in a joint of a human. The pain is perceived by the mammal to emanate from the joint and the tissues surrounding the joint.

The term "subject" includes mammals, including humans and other animals, such as domestic animals (e.g., household pets including cats and dogs) and non-domestic animals (such as wildlife). Preferably, the subject is a human patient.

The term "baseline" refers to that information which is gathered at the beginning of a treatment from which variations found in the study are measured. Baseline can also be described as a known value or quantity with which an unknown is compared when measured or assessed.

The term "AE" refers to adverse event.

The term "AUC" refers to area under the plasma concentration-time curve.

The term "$AUC_{0\text{-}tlast}$" refers to area under the plasma concentration-time curve from time zero up to the last quantifiable concentration.

The term "$AUC_{0\text{-}72h}$" refers to area under the plasma concentration-time curve from time zero up to 72 hours post-dose.

The term "$AUC_{0\text{-}\infty}$" refers to area under the plasma concentration-time curve from time zero to infinity.

The term "$EAUC_{0\text{-}24h}$" refers to area under the effect-time curve from time zero to 24 hours post dose.

The term "$EAUC_{0\text{-}336h}$" refers to area under the effect-time curve from time zero to 336 hours.

The term "$E_{avg0\text{-}24h}$" refers to the average $PGE_2$ inhibition over 24 hours.

The term "$E_{baseline}$" refers to baseline concentration.

The term "$E_{peak}$" refers to maximum effect.

The term "$ET_{max}$" refers to time to reach maximum effect.

The term "$t_{1/2}$" refers to apparent plasma terminal elimination half-life.

The mPGES-1 Inhibitor

Suitable mPGES-1 inhibitors include, but are not limited to, those disclosed in International Publication No. WO 2013/186692 ("the '692 Application"), which is hereby incorporated by reference in its entirety. These mPGES-1 inhibitors are useful for the treatment of pain and inflammation in a variety of diseases and conditions. One mPGES-1 inhibitor disclosed in the '692 Application is N-(4-chloro-3-(5-oxo-1-(4-(trifluoromethyl)phenyl)-4,5-dihydro-1H-1,2,4-triazol-3-yl)benzyl)pivalamide ('Compound I') having the structural formula:

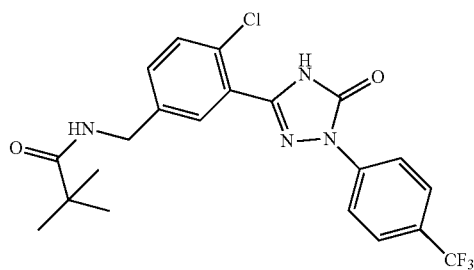 [SMILES: CC(C)(C)C(=O)NCc1ccc(Cl)c(-c2nn(-c3ccc(C(F)(F)F)cc3)c(=O)[nH]2)c1]

or its pharmaceutically acceptable salt.

Pharmaceutical Compositions

The pharmaceutical compositions described herein may be administered by oral, parenteral, inhalation, transdermal, transmucosal and nasal routes of administration, among others. Preferably, the pharmaceutical composition is administered orally.

The pharmaceutical compositions described herein may contain about 10 mg, about 20 mg, about 25 mg, about 30 mg, about 50 mg, about 75 mg, about 90 mg, about 120 mg, about 150 mg, about 180 mg, about 200 mg, about 250 mg, about 300 mg, about 350 mg, about 400 mg, about 450 mg, or about 500 mg of Compound I, or its pharmaceutically acceptable salt.

The pharmaceutical compositions for oral administration may be in various forms, for example, tablets, capsules, granules (synonymously, "beads" or "particles" or "pellets"), solution, suspension, emulsions, powders, dry syrups, and the like. In one embodiment, the pharmaceutical composition for oral administration is in the form of granules, tablets or capsules. In a preferred embodiment, the pharmaceutical composition for oral administration is in the form of a tablet.

The pharmaceutical compositions described herein may be prepared by methods known to those skilled in the art. In one embodiment, the present invention relates to a process for preparation of a pharmaceutical composition comprising Compound I, or its pharmaceutically acceptable, and optionally one or more pharmaceutically acceptable excipients, the process comprising admixing Compound I, or its pharmaceutically acceptable salt with the one or more pharmaceutically acceptable excipients to form a pharmaceutical composition.

The process for making the pharmaceutical composition may, for example, include, (1) granulating the active ingredient with the one or more pharmaceutically acceptable excipients to obtain granulate, and (2) converting the formed granulate into a suitable dosage form for oral administration.

The following examples are provided to enable one skilled in the art to practice the invention and are merely illustrative of the invention. The examples should not be read as limiting the scope of the invention.

EXAMPLES

Example 1

A three-part Phase I study of orally administered Compound I was conducted to evaluate the safety, tolerability and pharmacokinetics (PK) of single ascending doses in healthy, adult subjects (Part 1a), and of a single dose in elderly subjects (Part 2); the effect of food on PK (Part 1b) in healthy, adult subjects; and to compare the effects on prostanoid metabolism with celecoxib (Part 3) in healthy, adult subjects.

Objectives:

The primary objectives of the study were:

Part 1a (single ascending dose)—safety and tolerability of single ascending doses of Compound I in healthy adult subjects;

Part 1b (food effect)—effect of food on plasma pharmacokinetic (PK) of Compound I in healthy adult subjects;

Part 2 (elderly subjects)—tolerability of a single oral dose of Compound I in elderly subjects; and Part 3 (prostanoid metabolism)—to compare the effects of Compound I and celecoxib on urinary markers of prostanoid metabolism in healthy adult subjects.

Methodology:

Part 1 was a single-ascending-dose, double-blind, sequential-group study in healthy subjects (Part 1a), including a single-sequence crossover study of selected cohorts to evaluate the food effect (Part 1b).

Part 2 was a single-dose, double-blind study in a single cohort of elderly subjects. Part 3 was an open-label, randomized, 2-period, single-dose, crossover study to compare effects of the highest tolerated Compound I dose and celecoxib on prostanoid metabolism in healthy adult subjects.

Number of Subjects (Planned and Analyzed):

In Part 1a, it was planned to study 48 subjects, in 6 groups of 8. 48 subjects entered and completed the study.

In the food effect Part 1b, it was planned that 12 subjects in 2 groups from Part 1a who completed the fasting period would enter the fed period; 1 subject withdrew prior to the fed period, with 11 subjects completing the fed period. In Part 2, it was planned to study 8 subjects in 1 group, and 8 subjects entered and completed the study. In Part 3, it was planned for 20 subjects in 1 group, and 20 subjects entered and completed the study.

Diagnosis and Main Criteria for Inclusion:

Part 1 and Part 3 included healthy male or female subjects aged≥18 to ≤55 years, and Part 2 included healthy male or female subjects aged≥65 years.

Test Product, Dose and Mode of Administration, Batch Number:

In Part 1a, single doses of Compound I of 10 mg (Group A), 30 mg (Group B), 100 mg (Group C), 250 mg (Group D), 500 mg (Group E) and 1000 mg (Group F) were administered after fasting. In each dose group, 6 subjects received Compound I and 2 subjects received placebo.

In Part 1b, Compound I doses of 100 and 250 mg (Groups C and D) were administered after a meal; 5 subjects received 100 mg Compound I, 6 subjects received 250 mg Compound I, and 2 subjects received placebo.

In Part 2, a dose of 250 mg was administered after fasting. 6 subjects received Compound I and 2 subjects received placebo.

In Part 3, Compound I was administered at a dose of 1000 mg after fasting. All subjects received Compound I and all subjects received 400 mg celecoxib in a cross-over study design.

Duration of Treatment:

Single oral doses were administered to all subjects. In Part 1, subjects in Groups C and D, received a single oral dose after fasting in Part 1a and a single oral dose after a meal in Part 1b.

Criteria for Evaluation:

Pharmacokinetics:

Blood and urine samples for the analysis of plasma and urinary concentrations of Compound I.

Pharmacodynamics:

In Parts 1a and 3, whole blood samples were incubated and analyzed for lipopolysaccharide (LPS)-induced prostaglandin $PGE_2$ release. In Part 3, urine samples were collected for analysis of prostanoid metabolites.

Safety:

Adverse events (AEs), vital signs, 12-lead electrocardiogram (ECG), clinical laboratory evaluations and physical examination.

Statistical Methods:

Summary statistics were presented for the PK, pharmacodynamic (PD) and safety data, as appropriate. PK parameters following single oral doses of Compound I were determined from the plasma concentrations of Compound I using non-compartmental procedures in WinNonlin Dose proportionality was assessed using a power model, with $t_{max}$ analyzed using the Kruskal-Wallis test. The effect of food on PK was assessed at the 100 and 250 mg doses using a mixed effects model. The effect of age on PK was assessed for elderly (>65 years) versus non-elderly (<65 years) at the 250 mg dose level in Parts 1a and 2, using an analysis of variance (ANOVA) with age as a fixed effect. For PD analyses, percent decrease of ex vivo LPS-induced $PGE_2$ release was calculated. For Part 3, urinary excretion of prostanoid metabolites was also evaluated. The data are presented as absolute, as well as creatinine normalized urinary biomarker amounts, along percent change from baseline over a definite time interval. The percent change from baseline in urinary biomarkers was assessed using an analysis of covariance (ANCOVA) model Results:

Safety:

Single doses up to 1000 mg were well tolerated by healthy adult subjects. There was no evidence of a dose effect on incidence or severity of treatment-emergent AEs. No clinically significant lab abnormalities or ECG findings were observed.

Pharmacokinetics:

Following single oral doses of Compound I, there was rapid absorption at the 10 and 30 mg doses (median $T_{max}$ 2 hours) and steady absorption at doses of 100 to 1000 mg. The mean $T_{1/2}$ ranged from 41.7 to 54.5 hours and was independent of dose.

Near proportional increases in Compound I was observed over the 10 to 250 mg dose range while at higher doses (250 to 1000 mg) sub-proportional increases were observed. No notable pharmacokinetic differences or any biochemical or liver enzyme markers were observed in elderly subjects.

Inhibition of Ex-Vivo LPS-Induced $PGE_2$ Release:

Percent change in ex vivo LPS-induced $PGE_2$ release in whole blood is the pharmacodynamic (PD) biomarker. The $PGE_2$ levels in whole blood were estimated using the homogeneous time-resolved fluorescence method. PD parameters ($EAUC_{0-336h}$, $E_{baseline}$, $EAUC_{0-24h}$ and $E_{peak}$, and $ET_{max}$) were estimated using percent decrease (percent inhibition) from baseline (mean of Day −1 and predose).

Following single oral doses of Compound I from 10 mg to 1000 mg, there was a marked dose-dependent inhibition of ex vivo LPS-induced $PGE_2$ release. The reduction in $PGE_2$ release was apparent for approximately 24 hours post-dose with the lower doses, and was maintained for longer periods with higher doses. Near maximal inhibition was retained for at least 168 hours at the 250 and 500 mg doses and still apparent at 336 hours following the 1000 mg Compound I dose. $EAUC_{0-336h}$, $EAUC_{0-24h}$ and the maximum inhibition ($E_{peak}$) were statistically significantly different from placebo. FIG. 1 shows the percentage inhibition from baseline of ex vivo LPS-stimulated $PGE_2$ concentration following single oral doses of Compound I in healthy fasted subjects.

Concentrations below the limit of quantification were treated as ½ the lower limit of quantification for calculation.

Time points where unstimulated $PGE_2$ concentration was more than 3 times greater than the mean unstimulated $PGE_2$ and equal to or greater than ½ baseline value for an individual subject were not included in the calculation of percent inhibition. If pre-dose LPS-induced $PGE_2$ was less than unstimulated $PGE_2$, the value was not used for calculation of percent inhibition. Table 1 shows a summary of the PD analysis of Compound I evaluated in Part 1a of the study.

TABLE 1

Analysis of % Inhibition of Ex Vivo LPS-Induced PGE2 Release following Single Oral Doses of Compound I or Placebo in Fasted Healthy Subjects

| Parameter | | Placebo (N = 12) | Dose of Compound I | | | | | |
|---|---|---|---|---|---|---|---|---|
| | | | 10 mg (N = 6) | 30 mg (N = 6) | 100 mg (N = 6) | 250 mg (N = 6) | 500 mg (N = 6) | 1000 mg (N = 6) |
| $EAUC_{0-336\,h}$ (% · h) | LS mean | 1497[a] | −3824 | 8736 | 11612 | 14461 | 17914 | 19277 |
| | Difference in LS mean[b] | | −5321 | 7240 | 10115 | 12965 | 16417 | 17780 |
| | 95% CI for difference[b] | | −14306 to 3665 | −1746 to 16225 | 1130 to 19101 | 3979 to 21950 | 7432 to 25403 | 8795 to 26766 |
| | p-value for difference[b] | | 0.238 | 0.111 | 0.028 | 0.006 | <0.001 | <0.001 |
| $EAUC_{0-24\,h}$ (% · h) | LS mean | −58.5 | 898 | 970 | 1650 | 1550 | 1707 | 1028 |
| | Difference in LS mean[b] | | 956 | 1028 | 1709 | 1608 | 1766 | 1086 |
| | 95% CI for difference[b] | | 239 to 1674 | 311 to 1746 | 991 to 2426 | 891 to 2326 | 1048 to 2483 | 369 to 1804 |
| | p-value for difference[b] | | 0.010 | 0.006 | <0.001 | <0.001 | <0.001 | 0.004 |
| $E_{peak}$ (%) | LS mean | 67.8 | 77.7 | 72.8 | 91.6 | 92.8 | 87.7 | 81.8 |
| | Difference in LS mean[b] | | 9.90 | 4.94 | 23.8 | 24.9 | 19.9 | 14.0 |
| | 95% CI for difference[b] | | −3.94 to 23.7 | −8.90 to 18.8 | 9.94 to 37.6 | 11.1 to 38.8 | 6.04 to 33.7 | 0.125 to 27.8 |
| | p-value for difference[b] | | 0.156 | 0.475 | 0.001 | <0.001 | 0.006 | 0.048 |
| $ET_{max}$[c] (h) | Median | 12.0 | 4.00 | 3.04 | 7.02 | 2.03 | 12.0 | 144 |
| | Median difference[b] | | −8.02 | −8.98 | −7.50 | −9.94 | −0.0333 | 112 |
| | 95% CI for difference[b] | | −92.0 to −2.00 | −93.9 to −4.00 | −94.0 to 9.98 | −94.0 to −0.0167 | −84.0 to 36.0 | 24.0 to 160 |
| | p-value for difference[b] | | 0.010 | 0.005 | 0.220 | 0.027 | 0.777 | 0.027 |

[a]N = 11 for $EAUC_{0-336\,h}$
[b]versus placebo
[c]Median, median difference from placebo and approximate 95% CI
Concentrations below the limit of quantification were treated as ½ the lower limit of quantification for calculation.
Abbreviations:
CI = confidence interval;
LS = least squares;
N = number of subjects.

In part 3, following a single oral dose of Compound I at 1000 mg, there was a marked inhibition of LPS-induced $PGE_2$ concentration, where approximately 50% inhibition is maintained for at least 168 hours post-dose. Following a single oral dose of Celecoxib at 400 mg, maximal inhibition appeared similar to that attained with Compound I, although the duration of effect was considerably shorter, with no inhibition seen from 48 hours post-dose onwards. The results are shown in Table 2 below.

TABLE 2

Analysis of % Inhibition of Ex Vivo LPS-Induced PGE2 Release following Single Oral Doses of Compound I or Celecoxib in Fasted Healthy Subjects

| Parameter | | Celecoxib 400 mg (N = 20) | Compound I 1000 mg (N = 20) |
|---|---|---|---|
| $EAUC_{0-336\,h}$ (% · h) | LS mean | $-10159^a$ | 8866 |
| | Difference in LS mean[b] | | 19024 |
| | 95% CI for difference[b] | | 8458 to 29591 |
| | p-value for difference[b] | | <0.001 |
| $EAUC_{0-24\,h}$ (% · h) | LS mean | 1421 | 1428 |
| | Difference in LS mean[b] | | 7.89 |
| | 95% CI for difference[b] | | −194 to 210 |
| | p-value for difference[b] | | 0.935 |
| $E_{peak}$ (%) | LS mean | 89.1 | 87.2 |
| | Difference in LS mean[b] | | −1.87 |
| | 95% CI for difference[b] | | −5.09 to 1.36 |
| | p-value for difference[b] | | 0.239 |
| $ET_{max}^{c}$ (h) | Median | 6.00 | 12.0 |
| | Median difference[b] | | 6.00 |
| | 95% CI for difference[b] | | 0.0500 to 24.0 |
| | p-value for difference[b] | | 0.003 |

[a] N = 18 for $EAU_{0-336\,h}$
[b] versus celecoxib
[c] Median, median difference from celecoxib and approximate 95% CI Concentrations below the limit of quantification were treated as ½ the lower limit of quantification for calculation.

Time points where unstimulated prostaglandin E2 ($PGE_2$) concentration was more than 3 times greater than the mean unstimulated $PGE_2$ and equal to or greater than ½ baseline value for an individual subject were not included in the calculation of % inhibition.

Example 2

A two-part, Phase I study of orally administered Compound I was conducted to evaluate the safety, tolerability and pharmacokinetics of multiple ascending doses (MAD) in healthy subjects (Part 1), and of multiple doses in elderly subjects.

Objectives:

The primary objectives were:
Part 1 (MAD in healthy subjects)—to evaluate the safety and tolerability of multiple oral doses of Compound I in healthy adult subjects.
Part 2 (elderly subjects)—to evaluate the safety and tolerability of multiple oral doses of Compound I in elderly subjects.

The secondary objectives in Part 1 (MAD in healthy subjects) were to evaluate the:
plasma PK and cerebrospinal fluid (CSF) concentrations of Compound I following multiple doses to healthy adult subjects.
effect of multiple doses of Compound I on ex-vivo LPS-stimulated whole blood $PGE_2$ in healthy adult subjects.
effect of multiple doses of Compound I on urinary markers of prostanoid metabolism in healthy adult subjects.
effect of multiple doses of Compound I on urine 643 hydroxyl cortisol/cortisol molar ratio and plasma 4-13 hydroxycholesterol in healthy adult subjects.

The secondary objectives in Part 2 (Elderly subjects) were to evaluate the:
plasma PK of Compound I following multiple doses in elderly subjects.
effect of multiple doses of Compound I on urinary markers of prostanoid metabolism in elderly subjects.

Part 1:

Part 1 consisted of a MAD, double-blind, sequential-group study in healthy subjects. Twenty-four adult male and female subjects were recruited into 3 cohorts. Subjects were enrolled in a sequential manner in cohorts of 8, each randomized in a ratio of 6:2, to receive Compound I or placebo, respectively, for a duration of 28 days. Three dose levels of Compound I (25, 75 and 130 mg) were studied in Cohorts A, B and C, respectively. For each cohort in Part 1, the planned Compound I, qd dosing occurred in the fasted state in the morning on Days 1 to 28, both inclusive. Subjects in each cohort started dosing on the same day, with no less than 5 minutes dose interval between subjects on Day 1.

Part 2:

Part 2 consisted of a multiple dose, double-blind study in a single cohort of 8 elderly subjects, randomized in a ratio of 6:2 to receive Compound I or placebo, respectively, for a duration of 28 days. For the elderly cohort, 75 mg Compound I, q.d. dosing occurred in the fasted state in the morning on Days 1 to 28, both inclusive. For both parts of the study, subjects were screened within 28 days of dosing on Day 1. Enrolled subjects were admitted to the clinical research unit (CRU) on Day −2 for further eligibility checks. Each subject participated in 1 treatment period only, residing at the CRU from Day −2 (2 days before dosing) to Day 30 (48 hours after the last dose on Day 28). All subjects returned for non-residential visits on Days 31, 32, 33, 34 and 35, and for a final post-study visit on Day 42.

Inhibition of Ex-Vivo LPS-Induced $PGE_2$ Release:

Following multiple oral doses of Compound I from 25 mg to 130 mg qd, there was a marked drug-related inhibition of ex-vivo LPS-induced $PGE_2$ release on Days 1, 10 and 28. $EAUC_{0-24h}$, $E_{avg0-24h}$ and $E_{peak}$ were statistically significantly different from placebo for all Compound I doses on Days 1, 10 and 28, except for the comparison of $E_{peak}$ between 130 mg Compound I and placebo on Day 28. For each dose level, maximal inhibition was rapidly attained (being reached by the first sampling occasion of 30 minutes post-dose on Day 1) and was maintained over each 24-hour dosing period. The extent of inhibition of ex-vivo LPS-induced $PGE_2$ release was generally similar between doses and across study days. Statistical analysis generally showed no significant difference between days (Days 10 and 28 compared to Day 1) for each dose level (Table 3).

TABLE 3

Analysis of Percentage Inhibition of Ex Vivo LPS-Induced $PGE_2$ Release following Multiple Doses of Compound I or Placebo in Healthy Subjects

| Parameter | Day | Treatment | N | LS means | Difference in LS means (Compound I – placebo) | 95% CI for the difference (Compound I – placebo) lower | upper | p-value |
|---|---|---|---|---|---|---|---|---|
| $EAUC_{0-24\,h}$ (% · h) | 1 | Placebo qd | 6 | 337 | | | | |
| | | 25 mg qd | 6 | 1562 | 1225 | 627 | 1823 | <0.001 |
| | | 75 mg qd | 6 | 1555 | 1218 | 608 | 1828 | <0.001 |
| | | 130 mg qd | 6 | 1369 | 1032 | 433 | 1630 | 0.001 |
| | 10 | Placebo qd | 6 | −18.1 | | | | |
| | | 25 mg qd | 6 | 1443 | 1461 | 863 | 2059 | <0.001 |
| | | 75 mg qd | 6 | 1542 | 1560 | 950 | 2170 | <0.001 |
| | | 130 mg qd | 6 | 1374 | 1392 | 793 | 1990 | <0.001 |
| | 28 | Placebo qd | 6 | 340 | | | | |
| | | 25 mg qd | 6 | 1621 | 1281 | 682 | 1879 | <0.001 |
| | | 75 mg qd | 6 | 1696 | 1356 | 746 | 1966 | <0.001 |
| | | 130 mg qd | 6 | 1531 | 1192 | 593 | 1790 | <0.001 |
| $E_{avg0-24\,h}$ (%) | 1 | Placebo qd | 6 | 14.2 | | | | |
| | | 25 mg qd | 6 | 65.7 | 51.6 | 26.5 | 76.6 | <0.001 |
| | | 75 mg qd | 6 | 65.4 | 51.2 | 25.7 | 76.8 | <0.001 |
| | | 130 mg qd | 6 | 57.6 | 43.5 | 18.4 | 68.5 | 0.001 |
| | 10 | Placebo qd | 6 | −0.758 | | | | |
| | | 25 mg qd | 6 | 60.6 | 61.3 | 36.3 | 86.4 | <0.001 |
| | | 75 mg qd | 6 | 64.7 | 65.4 | 39.9 | 91.0 | <0.001 |
| | | 130 mg qd | 6 | 57.6 | 58.4 | 33.3 | 83.5 | <0.001 |
| | 28 | Placebo qd | 6 | 14.2 | | | | |
| | | 25 mg qd | 6 | 67.5 | 53.4 | 28.3 | 78.4 | <0.001 |
| | | 75 mg qd | 6 | 70.6 | 56.4 | 30.9 | 82.0 | <0.001 |
| | | 130 mg qd | 6 | 63.8 | 49.6 | 24.5 | 74.7 | <0.001 |
| $E_{peak}$ (%) | 1 | Placebo qd | 6 | 55.4 | | | | |
| | | 25 mg qd | 6 | 90.4 | 35.0 | 17.2 | 52.8 | <0.001 |
| | | 75 mg qd | 6 | 82.1 | 26.7 | 8.56 | 44.9 | 0.005 |
| | | 130 mg qd | 6 | 77.8 | 22.3 | 4.52 | 40.2 | 0.015 |
| | 10 | Placebo qd | 6 | 38.7 | | | | |
| | | 25 mg qd | 6 | 83.7 | 45.0 | 27.2 | 62.8 | <0.001 |
| | | 75 mg qd | 6 | 81.4 | 42.7 | 24.6 | 60.9 | <0.001 |
| | | 130 mg qd | 6 | 79.6 | 40.9 | 23.1 | 58.7 | <0.001 |
| | 28 | Placebo qd | 6 | 66.2 | | | | |
| | | 25 mg qd | 6 | 84.2 | 18.0 | 0.207 | 35.8 | 0.047 |
| | | 75 mg qd | 6 | 87.4 | 21.2 | 3.05 | 39.4 | 0.023 |
| | | 130 mg qd | 6 | 80.1 | 13.9 | −3.94 | 31.7 | 0.124 |
| $ET_{max}^{a}$ (h) | 1 | Placebo qd | 6 | 12.0 | | | | |
| | | 25 mg qd | 6 | 6.00 | −6.00 | −17.9 | 5.50 | 0.051 |
| | | 75 mg qd | 6 | 23.8 | 5.77 | −0.133 | 11.8 | 0.506 |
| | | 130 mg qd | 6 | 4.00 | −10.0 | −21.8 | 5.50 | 0.189 |
| | 10 | Placebo qd | 6 | 12.0 | | | | |
| | | 25 mg qd | 6 | 5.00 | −7.00 | −11.8 | 0 | 0.060 |
| | | 75 mg qd | 6 | 12.0 | −0.0333 | −11.8 | 4.00 | 0.346 |
| | | 130 mg qd | 6 | 4.00 | −6.03 | −17.8 | −2.00 | 0.012 |
| | 28 | Placebo qd | 6 | 12.0 | | | | |
| | | 25 mg qd | 6 | 2.00 | −6.00 | −10.0 | 1.00 | 0.270 |
| | | 75 mg qd | 6 | 10.0 | 0.0333 | −4.00 | 10.0 | 0.560 |
| | | 130 mg qd | 6 | 12.0 | 0.177 | −5.98 | 12.0 | 0.392 |

Concentrations below the limit of quantification were treated as ½ the lower limit of quantification for subsequent calculations.

Time points where unstimulated $PGE_2$ levels were 3 times greater than the mean of unstimulated $PGE_2$ and greater than or equal to half of the baseline for a particular subject were not included in the calculation of these parameters.

Baseline is the mean of Day −1 and pre-dose LPS stimulated $PGE_2$.

Abbreviations: CI=confidence interval; $EAUC_{0-24h}$=area under the effect-time curve from time zero to 24 hours postdose; $E_{avg0-24h}$=the average $PGE_2$ inhibition over 24 hours; $E_{peak}$=maximum effect; $ET_{max}$=time to reach maximum effect; LS=least squares; N=number of subjects; $PGE_2$=prostaglandin E2; qd=once daily.

[a] Median, median difference from placebo and approximate 95% CI.

Example 3

A Phase II Dose Range Finding 12-week, Double-Blind, Randomized, Parallel Group Study to Evaluate Safety and Efficacy of Compound I in Patients with Moderate Osteoarthritis Pain.

The study is performed in accordance with International Conference on Harmonization (ICH), Good Clinical Practice (GCP) guidelines, ethical principles as per Declaration of Helsinki and guidelines for Clinical Trials on Pharmaceutical Products in India—GCP issued by the Central Drugs Standard Control Organization, Ministry of Health, and Government of India.

Objectives:
 To evaluate the efficacy of Compound I given orally at daily doses of 10 mg, 25 mg and 75 mg for 12-weeks compared to placebo, in patients with moderate osteoarthritis pain.
 To evaluate safety and tolerability of Compound I given orally at daily doses of 10 mg, 25 mg and 75 mg for 12-weeks compared to placebo, in patients with moderate osteoarthritis pain.
 To evaluate the pharmacokinetics of Compound I and its metabolite(s), with Compound I given orally at daily doses of 10 mg, 25 mg and 75 mg in patients with moderate osteoarthritis pain.
 To evaluate the effect of Compound I on ex-vivo lipopolysaccharide (LPS)-stimulated prostaglandin E2 ($PGE_2$) release in whole blood and assess pharmacokinetic and pharmacodynamic relationship.

Study Design:
 This is a four-arm, randomized, double-blind, double dummy, parallel group, placebo-controlled study. The study comprises three study periods: screening including wash out (2 weeks), double-blind treatment period (12 weeks) and a follow up (2 weeks).
 After giving written informed consent, men and women subjects aged 40 to 70 years (both inclusive) with a confirmed clinical & radiological diagnosis of primary osteoarthritis of the hip or knee, according to American college of Rheumatology (ACR) criteria 10, 11 and who have been symptomatic for at least 3 months prior to enrolment and who may or may not have received an NSAID or other oral analgesic therapy are recruited.
 Subjects who have not received any oral NSAIDs or other analgesic treatment for a period of at least 1 week prior to screening, must report moderate pain intensity defined as minimum of 40 mm and maximum of 74 mm on 0-100 Visual Analogue Scale (Pain Walking on a Flat Surface. WOMAC 3.1, Section A, Question 1). Subjects receiving an oral NSAID for a period of at least 2 weeks prior to screening, are asked to undergo a washout period of up to 7 days or 5 half-lives, during which all pain medications are discontinued. Subjects who have received prior oral NSAIDs must report moderate pain intensity at defined as minimum of 40 mm and maximum of 74 mm on 0-100 Visual Analogue Scale (Pain Walking on a Flat Surface. WOMAC 3.1, Section A, Question 1) and a minimum increase of 15 mm compared to screening in the most severely affected joint during the 24 hours prior to randomization. The joint assessed to be the most severely affected at screening, are evaluated throughout the study.
 Eligible subjects are randomly assigned to one of the following arms in a double-dummy, double blind design with a 1:1:1:1 ratio. Randomization across the treatment arms is balanced for subjects having received previous NSAIDs as well as those who receive background treatment with chondroprotective agents.
  Arm 1: Compound I, 10 mg, QD for 12 weeks
  Arm 2: Compound I, 25 mg, QD for 12 weeks
  Arm 3: Compound I, 75 mg, QD for 12 weeks
  Arm 4: Placebo, QD for 12 weeks
 Subjects undergo 7 visits; a screening visit, baseline/randomization visit, visits at weeks 2, 4, 8, 12 and a follow up visit 2 weeks after the last dose of the study drug. Efficacy assessments are performed at weeks 2, 4, 8, 12 and follow up visit. A small subset of consenting subjects participate in PK/PD sub study (up to 20 subjects per treatment group for PK and up to 10 subjects per treatment group for PD) and serial blood samples for PK and PD are collected from these subjects at certain time points.
 Subjects who experience protocol defined significant worsening in pain are allowed to use paracetamol up to a maximum of 2.6 g/day as a rescue analgesic during the washout period as well as throughout the study treatment period.

Criteria for Inclusion of Subjects:
 Male and female subjects 40 to 70 years of age diagnosed with primary osteoarthritis of the hip or knee for at least 3 months in accordance with American College of Rheumatology (ACR) clinical and radiological criteria.
 Subjects who have not received any oral NSAIDs or other analgesic treatment for a period of at least 1 week prior to screening, must report moderate pain intensity at visits 1 and 2 defined as minimum of 40 mm and maximum of 74 mm on 0-100 Visual Analogue Scale (Pain Walking on a Flat Surface. WOMAC 3.1, Section A, Question 1) in the most severely affected joint.
 Subjects who have received prior oral NSAIDs and/or other oral analgesic medication for at least 2 weeks at the time of screening, must report moderate pain intensity at visit 2 defined as minimum of 40 mm and maximum of 74 mm on 0-100 Visual Analogue Scale (Pain Walking on a Flat Surface. WOMAC 3.1, Section A, Question 1) and a minimum increase of 15 mm compared to screening visit in the most severely affected joint.

Clinical Endpoints:
 Mean change from baseline in the Western Ontario and McMaster's University Osteoarthritis Index 3.1 pain subscale (WOMAC-PS) at the end of 12 weeks of treatment.
 Mean change from baseline in the WOMAC-3.1 pain subscale at the end of 2, 4 and 8 weeks of treatment and at follow up (14 weeks).
 Mean change from baseline in the WOMAC-3.1 physical function subscale (WOMAC-PFS) at the end of 2, 4, 8 and 12 weeks of treatment and at follow up (14 weeks).
 Mean change from baseline in overall WOMAC-3.1 index at the end of 2, 4, 8 and 12 weeks of treatment and at follow up (14 weeks).
 Mean change from baseline in the Patient Global Assessment of Response to Therapy (PGART) using 0-4 point Likert scale at the end of 2, 4, 8 and 12 weeks of treatment and at follow up (14 weeks).
 Mean change from baseline in the Investigator Global Assessment of Response to Therapy (IGART) using 0-4 point Likert scale at the end of 2, 4, 8 and 12 weeks of treatment and at follow up (14 weeks).
 Proportion of subjects discontinuing due to lack of efficacy and/or requiring rescue medication use for pain in affected joint.
 Proportion of subjects meeting OMERACT-OARSI responder criteria at the end of 4, 12 weeks.
 Incidence of TEAEs and SAEs (including AEs special interest such as edema, hypertension, congestive heart failure, pulmonary edema, cardiac failure, pre-defined upper GI events and CV events).
 Maximum plasma concentration ($C_{max}$), time to attain $C_{max}$ ($T_{max}$) and area under the plasma concentration-time curve over the dosing interval ($AUC_{0-tau}$) for Compound I on Day 1 and Day 85 based on the Pharmacokinetic Analysis Set (PKAS).
 Mean change in ex vivo LPS-stimulated whole blood $PGE_2$ release from baseline on Day 1 and Day 85 of dosing.

What is claimed is:

1. A method of treating osteoarthritis pain in a subject in need thereof, the method comprising orally administering to the subject from about 10 mg to about 1000 mg of a pharmaceutical composition per day, the composition comprising N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof, wherein the pharmaceutical composition is a nanoparticulate composition.

2. The method according to claim 1, wherein the method comprises orally administering a nanoparticulate pharmaceutical composition comprising about 10 mg of N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof.

3. The method according to claim 1, wherein the method comprises orally administering a nanoparticulate pharmaceutical composition comprising about 25 mg of N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof.

4. The method according to claim 1, wherein the method comprises orally administering a nanoparticulate pharmaceutical composition comprising about 75 mg of N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof.

5. The method according to claim 1, wherein the subject exhibits primary osteoarthritis of the hip or knee for at least 3 months in accordance with American College of Rheumatology (ACR) clinical and radiological criteria.

6. The method according to claim 1, wherein the subject has moderate pain intensity defined as a minimum of 40 mm and a maximum of 74 mm on 0-100 Visual Analogue Scale (Pain Walking on a Flat Surface, WOMAC 3.1, Section A, Question 1) in the most severely affected joint.

7. The method according to claim 1, wherein the subject exhibits more than a 30% reduction from baseline in the Western Ontario and McMaster's University Osteoarthritis Index 3.1 pain subscale (WOMAC-PS) upon treatment with N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof.

8. The method according to claim 1, wherein the subject exhibits a mean change from baseline in the Western Ontario and McMaster's University Osteoarthritis Index 3.1 pain subscale (WOMAC-PS) at the end of 12 weeks of treatment.

9. The method according to claim 1, wherein the subject exhibits a mean change from baseline in overall WOMAC-3.1 index at the end of 2, 4, 8 and 12 weeks of treatment.

10. The method according to claim 1, the method comprising orally administering a nanoparticulate pharmaceutical composition comprising about 10 mg to about 100 mg of N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof, wherein the subject has moderate pain intensity defined as a minimum of 40 mm and a maximum of 74 mm on 0-100 Visual Analogue Scale (Pain Walking on a Flat Surface, WOMAC 3.1, Section A, Question 1) in the most severely affected joint.

11. The method according to claim 1, the method comprising orally administering a nanoparticulate pharmaceutical composition comprising about 10 mg, about 25 mg or about 75 mg of N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof, wherein the subject has moderate pain intensity defined as a minimum of 40 mm and a maximum of 74 mm on 0-100 Visual Analogue Scale (Pain Walking on a Flat Surface, WOMAC 3.1, Section A, Question 1) in the most severely affected joint.

12. The method according to claim 1, the method comprising orally administering a nanoparticulate pharmaceutical composition comprising about 10 mg of N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof, wherein the subject has moderate pain intensity defined as a minimum of 40 mm and a maximum of 74 mm on 0-100 Visual Analogue Scale (Pain Walking on a Flat Surface, WOMAC 3.1, Section A, Question 1) in the most severely affected joint.

13. The method according to claim 1, the method comprising orally administering a nanoparticulate pharmaceutical composition comprising about 25 mg of N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof, wherein the subject has moderate pain intensity defined as a minimum of 40 mm and a maximum of 74 mm on 0-100 Visual Analogue Scale (Pain Walking on a Flat Surface, WOMAC 3.1, Section A, Question 1) in the most severely affected joint.

14. The method according to claim 1, the method comprising orally administering a nanoparticulate pharmaceutical composition comprising about 75 mg of N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof, wherein the subject has moderate pain intensity defined as a minimum of 40 mm and a maximum of 74 mm on 0-100 Visual Analogue Scale (Pain Walking on a Flat Surface, WOMAC 3.1, Section A, Question 1) in the most severely affected joint.

15. The method according to claim 1, wherein the method comprises orally administering a nanoparticulate pharmaceutical composition comprising from about 10 to about 100 mg of N-(4-chloro-3-(5-oxo-1-(4-(trifluoromethyl)phenyl)-4,5-dihydro-1H-1,2,4-triazol-3-yl)benzyl)pivalamide, or a pharmaceutically acceptable salt thereof.

16. The method of claim 1, wherein the nanoparticulate pharmaceutical composition is administered once or twice daily.

17. The method of claim 1, wherein the osteoarthritis pain is moderate osteoarthritis pain.

* * * * *